(12) United States Patent
Cui et al.

(10) Patent No.: US 12,144,835 B2
(45) Date of Patent: Nov. 19, 2024

(54) COMBINATION DRUGS OF LACHNOSPIRACEAE BACTERIA AND HUMAN IMMUNOGLOBULIN

(71) Applicants: Institute of Radiation Medicine, Chinese Academy of Medical Sciences, Tianjin (CN); Institute of Blood Transfusion, Chinese Academy of Medical Sciences, Sichuan (CN); Shanghai RAAS Blood Products Co., Ltd., Shanghai (CN)

(72) Inventors: Ming Cui, Tianjin (CN); Zongkui Wang, Sichuan (CN); Changqing Li, Sichuan (CN); Jun Xu, Shanghai (CN); Lu Cheng, Shanghai (CN)

(73) Assignees: Institute of Radiation Medicine, Chinese Academy of Medical Sciences, Tianjin (CN); Institute of Blood Transfusion, Chinese Academy of Medical Sciences, Sichuan (CN); Shanghai RAAS Blood Products Co., Ltd., Shanghai (CN)

( * ) Notice: Subject to any disclaimer, the term of this patent is extended or adjusted under 35 U.S.C. 154(b) by 90 days.

(21) Appl. No.: 17/861,811

(22) Filed: Jul. 11, 2022

(65) Prior Publication Data
US 2022/0347233 A1 Nov. 3, 2022

(30) Foreign Application Priority Data
Jul. 13, 2021 (CN) .......................... 202110791991.X

(51) Int. Cl.
*A61K 35/741* (2015.01)
*A61K 35/16* (2015.01)
*A61P 39/00* (2006.01)

(52) U.S. Cl.
CPC ............ *A61K 35/741* (2013.01); *A61K 35/16* (2013.01); *A61P 39/00* (2018.01)

(58) Field of Classification Search
CPC ........ A61K 35/16; A61K 35/741; A61P 39/00
See application file for complete search history.

(56) References Cited

PUBLICATIONS

Wang et al, Sexual Dimorphism in Gut Microbiota Dictates Therapeutic Efficacy of Intravenous Immunoglobulin on Radiotherapey Complications, J Adv Res, Apr. 46: pp. 123-133. (Year: 2023).*
Guo, Hao et al., "Multi-omics analyses of radiation survivors identify radioprotective microbes and metabolites". Science, Oct. 30, 2020; vol. 370, Issue 6516; Oct. 30, 2020; DOI: 10.1126/science.aay9097; pp. 1-27.
Li, Yuan et al., "Gut commensal derived-valeric acid protects against radiation injuries", Gut Microbes, vol. 11; Jan. 13, 2020, pp. 789-806.

* cited by examiner

*Primary Examiner* — Carlos A Azpuru
(74) *Attorney, Agent, or Firm* — NKL Law; Allen Xue

(57) ABSTRACT

A combined drug contains Lachnospiraceae bacteria and human immunoglobulin (HIg). HIg has a therapeutic effect on radiation injuries, and the combination of Lachnospiraceae bacteria and HIg can further improve this therapeutic effect. The combination drug can be administered to patients who were undergoing radiotherapy and to people who accidentally receive excessive irradiation.

9 Claims, 4 Drawing Sheets

COMBINATION DRUGS OF LACHNOSPIRACEAE BACTERIA AND HUMAN IMMUNOGLOBULIN

TECHNICAL FIELD

The present invention belongs to the field of biopharmaceuticals.

BACKGROUND TECHNOLOGY

Cancer is the second leading cause of death in human beings. Radiotherapy is a widely used means for the treatment of cancer, and its contribution ratio to cancer treatment is as high as 18%, which is second only to surgery and significantly higher than chemotherapy and biological therapy. However, it is inevitable that radiotherapy is accompanied by varying degrees of acute and chronic organ damage represented by inflammation and by fibrosis, respectively. Specifically, radiotherapy for head and neck tumors often leads to oral mucositis; radiotherapy for thoracic tumors often leads to chronic pneumonia; and radiotherapy for abdominal and pelvic tumors often leads to diarrhea, chronic enteritis, intestinal obstruction, etc. However, hematopoietic injury such as leukocytopenia and myeloid deviation as well as digestive tract injury such as enteritis and intestinal obstruction are very common complications in radiotherapy for multiple cancers, which will halt radiotherapy prematurely, degrade patient life quality, and even cause death. Increasing the dose of radiation therapy will inevitably increase the risk of acute and chronic radiation damage to healthy organs. Therefore, reducing the acute and chronic radiation injuries associated with radiotherapy will promote the clinical application of radiotherapy to a greater extent and improve the prognosis and quality of life for cancer patients.

With the rapid development of nuclear technology and nuclear industry, nuclear energy has been widely used in industrial and agricultural production, scientific and technological research, national defense and people's wellbeing. The peaceful use of "nuclear" has become a driving force for the development of all countries in the world. Deviation from operating conditions in nuclear facilities or nuclear activities, that is, the occurrence of a nuclear accident, will cause accidental and involuntary exposure for workers and surrounding people, resulting in radiation injuries. Therefore, drugs for radiation injuries should be kept by people who live in the place near nuclear facilities.

HIg is an immunoglobulin product derived from healthy donor plasma pools by the procedures of separation, purification, and virus inactivation/removal, whose main active ingredient is a combination of polyclonal immunoglobulins against various exogenous antigens and self-antigens. The human immunoglobulin according to the administration route can be divided into intravenous immunoglobulin (IVIg), intramuscular immunoglobulin (IMIg) and subcutaneous immunoglobulin (SCIg). HIg is an effective drug for the treatment of primary immunodeficiency, secondary immunodeficiency, autoimmune diseases (Kawasaki disease, idiopathic thrombocytopenic purpura), and is widely used in clinical practice.

The present inventors have found that HIg had a certain therapeutic effect on radiation injuries, which was specifically shown that irradiation led to atrophy of thymus and spleen, reduction in the number of lymphocytes, shortening of the large intestine, and increase in the level of inflammation in the small intestine, as well as leading to death in mice exposed to radiation. On the other hand, HIg helped the mice to reverse the above symptoms and reduce the mortality. However, the effect of HIg is significant only in females, while its effect needs to be improved in males (patent application 202010925913.X).

Lachnospiraceae bacteria are a group of bacteria that can colonize in the intestinal tract and have been reported to have the ability to digest cellulose and hemicellulose originated from plants, so as to increase the bioavailability of food; the bacteria can also produce short-chain fatty acids as a major nutrient supply for intestinal epithelial cells. Hao Guo et al. have reported that a mixture of 23 Lachnospiraceae strains can be used to treat radiation injuries. However, the proportion of these 23 Lachnospiraceae strains is unclear, the preparation is complicated, and the therapeutic effect lowers with the decrease of Lachnospiraceae abundance (Guo H. et al., Multi-omics analyses of radiation survivors identify radioprotective microbes and metabolites. Science, Oct. 30, 2020; 370 (6516): eaay9097).

Content of the Invention

The object of the present invention is to provide a combined drug that enhances the efficacy of HIg in the treatment of radiation injuries.

In the present invention, "radiation injury" refers to the injuries resulted from irradiation of X-rays due to radiation therapy, accelerators, and $\alpha$, $\beta$ and/or $\gamma$ rays emitted by radioactive substances on the body, and said irradiation includes both irradiation on the surface of the body and irradiation on cells in the body after the radioactive substance enters the body. In the present invention, ATCC is an abbreviation for the American Type Culture Collection.

The technical solution of the present invention is as follows:

The present invention provides a combined drug for the treatment of radiation injuries, which contains Lachnospiraceae bacteria and human immunoglobulin (HIg) with the same or different specifications, that are administered simultaneously or separately;

said HIg includes intravenous immunoglobulin (IVIg), intramuscular immunoglobulin (IMIg) and/or subcutaneous immunoglobulin (SCIg).

Further, said Lachnospiraceae bacteria are those with ATCC number BAA-2278.

Further, said combined drug is the one that restores the hematopoietic function of the body after radiation injuries.

Further, said combined drug is the one that retards thymic atrophy, spleen atrophy, leukocytopenia and/or inflammation caused by radiation injuries.

Further, said inflammation is intestinal inflammation.

Further, said combined drug is for male (including human and animals).

The present invention further provides the use of said combined drug mentioned above in the preparation of a medicament for reducing radiation injuries.

The present invention provides a combined drug for treating tumors, which contains anti-tumor radiotherapy drugs, Lachnospiraceae bacteria and HIg with the same or different specifications, that are administered simultaneously or separately;

said IHIg includes intravenous immunoglobulin (IVIg), intramuscular immunoglobulin (IMIg) and/or subcutaneous immunoglobulin (SCIg).

Further, said Lachnospiraceae bacteria are those with ATCC number BAA-2278.

Further, said combined drug is the one that restores the hematopoietic function of the body after radiotherapy.

Further, said combined drug is the one that retards thymic atrophy, spleen atrophy, leukocytopenia and/or inflammation caused by radiation injuries.

Further, said inflammation is intestinal inflammation.

Further, said combined drug is for male (including human and animals).

The beneficial effects of the present invention include:

1) The combined drug of the present invention can be used to restore the hematopoietic function after radiation;

2) The combined drug of the present invention can alleviate thymic atrophy, spleen atrophy, leukocytopenia and/or inflammation caused by radiation;

3) The combined drug of the present invention can overcome the disadvantage that IVIg alone cannot effectively treat radiation injuries in male animals.

Obviously, based on the above content of the present invention, according to the common technical knowledge and the conventional means in the field, without department from the above basic technical spirits, other various modifications, alternations, or changes can further be made.

By the following specific examples of said embodiments, the above content of the present invention is further illustrated. But it should not be construed that the scope of the above subject matter of the present invention is limited to the following examples. The techniques realized based on the above content of the present invention are all within the scope of the present invention.

EXAMPLES

Example 1. Use of the Combination of IVIg+Lachnospiraceae for the Treatment of Radiation Injuries Lachnospiraceae used in this example are Lachnospiraceae bacteria with the number ATCC BAA-2278.

1. Method 1.1. Analysis of Hematopoietic System Injury by Total Body Irradiation at 5 Gy 24 male mice were divided into two groups:
1) IVIg group, 12 mice;
2) IVIg+Lachnospiraceae group, 12 mice;

IVIg was administrated to IVIg group within 5 min after total body irradiation, followed by injecting IVIg twice a week for two weeks at a dose of 0.3 g/kg body weight.

For IVIg+Lachnospiraceae group, Lachnospiraceae was orally given to mice within 30 min before total body irradiation, and then IVIg was administrated within 5 min after irradiation, followed by administrating IVIg twice a week for two weeks as well as orally giving Lachnospiraceae every two days. The dose of Lachnospiraceae was $1\times10^7$; while the dose of IVIg was 0.3 g/kg body weight.

1.2. Analysis of Intestinal Injury by 12 Gy of Local Abdominal Irradiation 44 male mice were divided into 4 groups:
1) TAI group, 10 mice;
2) Lachnospiraceae group, 10 mice;
3) IVIg group, 12 mice;
4) IVIg+Lachnospiraceae group, 12 mice;

TAI group received only local abdominal irradiation, and then PBS was injected to the mice in equal volume with other groups.

Lachnospiraceae was orally given to the mice in Lachnospiraceae group 30 min before local abdominal irradiation, followed by orally administration once every two days. The dose of Lachnospiraceae was $1\times10^7$.

IVIg was intravenously injected into the mice in IVIg group within 5 min after local abdominal irradiation, followed by injection twice a week for two weeks at a dose of 0.3 g/kg body weight. Lachnospiraceae was orally administrated to the mice in IVIg+Lachnospiraceae group 30 min before local abdominal irradiation, and then IVIg was intravenously injected within 5 min after irradiation, followed by injecting IVIg twice a week for two weeks as well as orally giving Lachnospiraceae every two days. The dose of Lachnospiraceae was $1\times10^7$; while the dose of IVIg was 0.3 g/kg body weight.

Then, peripheral blood was collected from mice to detect the number of white blood cells. Spleen, thymus and small intestine were taken for observation, and the levels of IL-6 and TNF-α in small intestine were further detected.

2. Results

Figure 1:
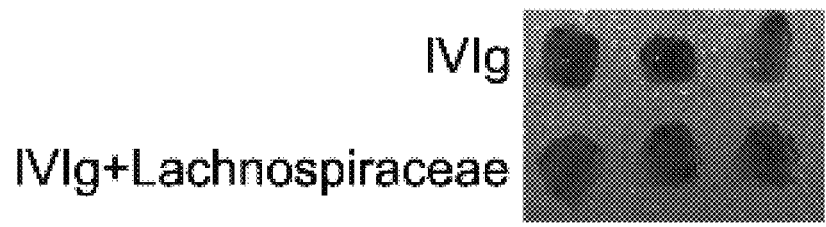
FIG. 1: The appearance of the thymus.
Figure 2:
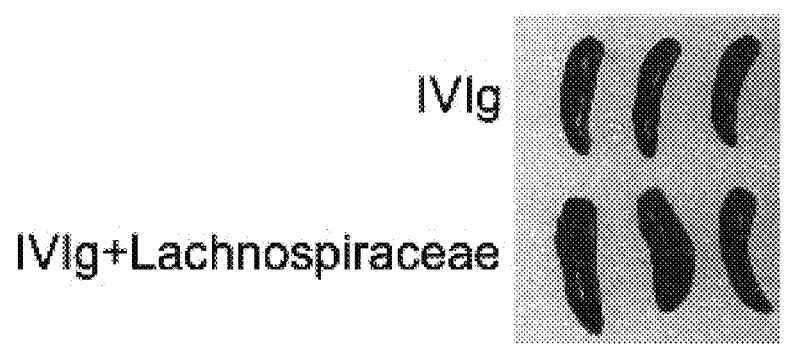
FIG. 2: The appearance of the spleen.
Figure 3:
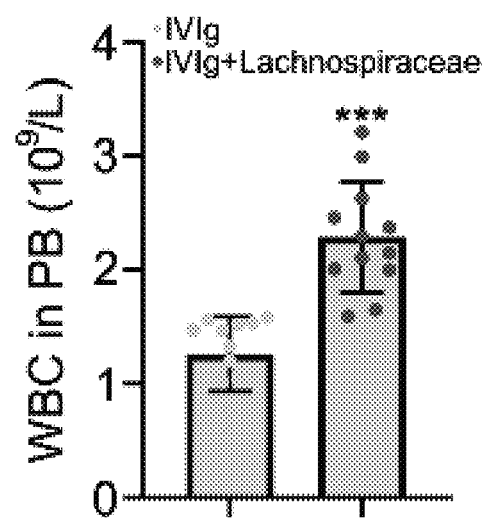
FIG. 3: Leukocyte count in peripheral blood.

Total body irradiation could lead to the atrophy of thymus and spleen, decrease in hematopoietic function, and subsequent reduction of white blood cells. As shown in FIGS. 1-3, the volumes of thymus and spleen as well as leukocyte numbers were significantly increased in IVIg+Lachnospiraceae group compared with IVIg group. The results indicated that the combination of IVIg and Lachnospiraceae could more obviously restore the size of thymus and spleen in mice compared with IVIg alone, and further lead to the recovery of hematopoietic function in irradiated mice.

Figure 4:
FIG. 4: The appearance of the large intestine in TAI group and Lachnospiraceae group.
Figure 5:
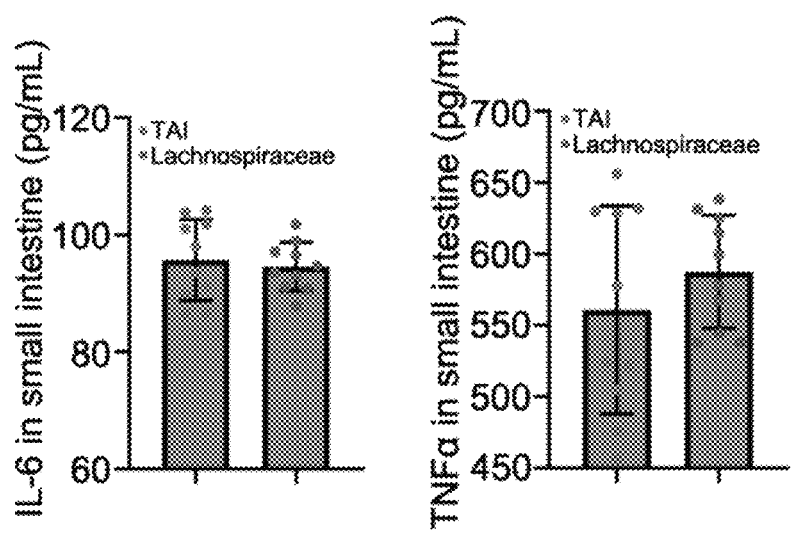
FIG. 5: Levels of TNF-α and IL-6 in the small intestine of TAI group and Lachnospiraceae group. The ordinate mL represents the volume of PBS used to extract TNF-α and IL-6 from the small intestine, and the volume of PBS used for each unit weight of the small intestine is consistent.
Figure 6:
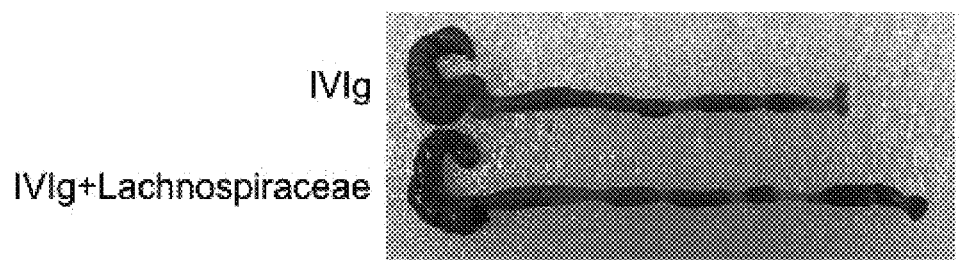
FIG. 6: The appearance of the large intestine in IVIg group and IVIg+Lachnospiraceae group.
Figure 7:
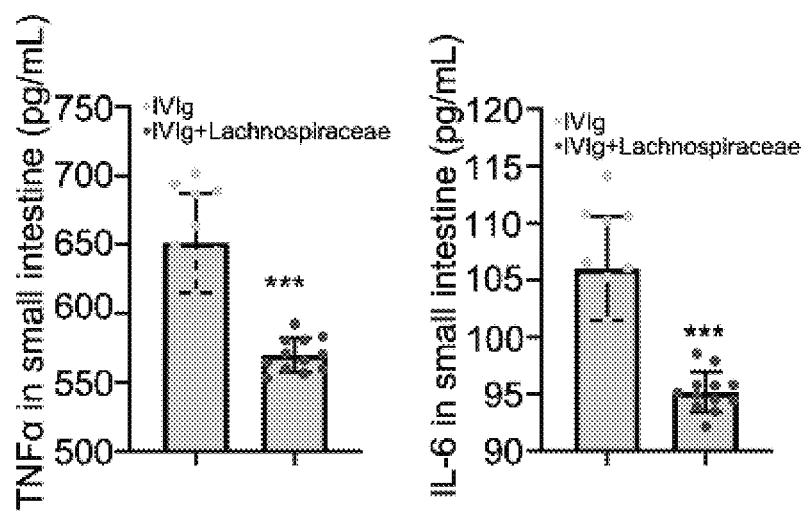
FIG. 7: Levels of TNF-α and IL-6 in the small intestine of IVIg group and IVIg+Lachnospiraceae group. The ordinate mL represents the volume of PBS used to extract TNF-α and IL-6 from the small intestine, and the volume of PBS used for each unit weight of the small intestine is consistent.

Local abdominal irradiation could result in the shortening of the large intestine and the elevation of inflammatory factors TNFα and IL-6 in the small intestine in mice, leading to the occurrence of enteritis (Li et al., Gut commensal derived-valeric acid protects against radiation injuries. Gut Microbes, 2020, 11: 789-806). The length of the large intestine and the levels of inflammatory factors TNFα and IL-6 in the small intestine did not differ from that of TAI group (FIGS. 4 and 5), indicating that oral administration of Lachnospiraceae alone could not inhibit the radiation-induced inflammation. As shown in FIG. 6, the length of the large intestine in IVIg+Lachnospiraceae group was longer than that in IVIg group, and the levels of inflammatory cytokines TNFα and IL-6 in the small intestine were also lower than that in IVIg group (FIG. 7). This suggested that compared with the single use of IVIg, the combination of IVIg and Lachnospiraceae could further inhibit the radiation-induced inflammation.

The results of this example showed that Lachnospiraceae alone could not inhibit the radiation-induced inflammation, and compared with the administration of IVIg alone, the combination of IVIg and Lachnospiraceae could further inhibit the radiation-induced inflammation. In summary, the combination drug of the present invention can be used to restore the hematopoietic function of the body after irradiation, and can alleviate the atrophy of thymus and spleen, leukocytopenia and/or inflammation caused by irradiation; and the combination drug has overcome the disadvantage that IVIg alone cannot effectively treat male animals.

The invention claimed is:

1. A combined drug for the treatment of radiation injuries in men, comprising Lachnospiraceae bacteria and human immunoglobulin (HIg), wherein said Lachnospiraceae bacteria and said HIg are administered simultaneously or separately; and said HIg includes intravenous immunoglobulin (IVIg), intramuscular immunoglobulin (IMIg) and/or subcutaneous immunoglobulin (SCIg).

2. The combined drug according to claim 1, wherein said Lachnospiraceae bacteria are those with ATCC number BAA-2278.

3. The combined drug according to claim 1, wherein said combined drug is the one that restores the hematopoietic function of the body after radiation injuries.

4. The combined drug according to claim 1, wherein said combined drug is the one that retards thymic atrophy, spleen atrophy, leukocytopenia and/or inflammation caused by radiation injuries.

5. A method for reducing radiation injuries, comprising administering an effective amount of a composition to a subject in need thereof, wherein the composition comprises a combined drug according to claim 1.

6. A combined drug for treating tumors in male subjects, comprising anti-tumor radiotherapy drugs, Lachnospiraceae bacteria and HIg, wherein said anti-tumor radiotherapy drugs, said Lachnospiraceae bacteria and said HIg are administered simultaneously or separately; and
    said HIg includes intravenous immunoglobulin (IVIg), intramuscular immunoglobulin (IMIg) and/or subcutaneous immunoglobulin (SCIg).

7. The combined drug according to claim 6, wherein said Lachnospiraceae bacteria are those with ATCC number BAA-2278.

8. The combined drug according to claim 6, wherein said combined drug is the one that restores the hematopoietic function of the body after radiotherapy.

9. The combined drug according to claim 6, wherein said combined drug is the one that retards thymic atrophy, spleen atrophy, leukocytopenia and/or inflammation caused by radiotherapy subject.

* * * * *